(12) United States Patent
Spahn

(10) Patent No.: US 6,477,228 B2
(45) Date of Patent: Nov. 5, 2002

(54) METHOD FOR OPERATING AN X-RAY DIAGNOSIS DEVICE WITH IMMEDIATE IMAGING

(75) Inventor: Martin Spahn, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/952,067

(22) Filed: Sep. 14, 2001

(65) Prior Publication Data

US 2002/0064315 A1 May 30, 2002

(30) Foreign Application Priority Data

Sep. 15, 2000 (DE) .......................................... 100 45 929

(51) Int. Cl.[7] ............................................. G01N 23/04
(52) U.S. Cl. ............................. 378/62; 378/51; 382/132
(58) Field of Search ...................... 378/62, 51; 382/299, 382/132

(56) References Cited

U.S. PATENT DOCUMENTS 5,617,461 A * 4/1997 Schreiner ................. 378/98.12
5,833,607 A * 11/1998 Chou et al. ................. 382/130

FOREIGN PATENT DOCUMENTS

EP 0 567 174 10/1993

OTHER PUBLICATIONS

Patent Abstracts of Japan: Publication No. 04287476, published Oct. 13, 1992; Application number 03051824; filed Mar. 18, 1991 "Exposure Device"; Inventor Nishiura et al.; Applicant Fujitsu Ltd. English Abstract, 1 sheet.

* cited by examiner

Primary Examiner—David V. Bruce
Assistant Examiner—Pamela R. Hobden
(74) Attorney, Agent, or Firm—Schiff Hardin & Waite

(57) ABSTRACT

The invention relates to a method for operating an X-ray diagnosis device for producing X-ray images using an X-ray appliance (1 to 5), for processing the X-ray images with a computation unit (7), and for displaying the X-ray images using a reproduction apparatus (8). According to the invention, the method has the following steps: preprocessing the X-ray images with parameters for full resolution; converting the X-ray images into images with low resolution; processing the images with low resolution with images and/or parameters matched to the reduced resolution; immediately reproducing the images with low resolution; subsequently processing the X-ray images with parameters for full resolution; and reproducing the X-ray images with full resolution.

7 Claims, 5 Drawing Sheets

METHOD FOR OPERATING AN X-RAY DIAGNOSIS DEVICE WITH IMMEDIATE IMAGING

SUMMARY OF THE INVENTION

1. Field of the Invention

The invention relates to a method for operating an X-ray diagnosis device for producing X-ray images using an X-ray appliance, for processing the X-ray images using a computation unit and for displaying the X-ray images using a reproduction apparatus.

2. Background of the Related Art

In X-ray departments for general radiography and for mammography, the capability to display the recorded image or images immediately is a major advantage in the course of X-ray examination (workflow). With the sheet-film or memory-film-based cassette systems that are normally used, several minutes typically pass before the image can be viewed. In one case, the film must be developed, and in the other case the memory film must be read in a reader. Until this has been done, it is impossible to decide whether the record has survived the recording technique, and the patient can leave the examination area. Additional time is therefore consumed in the event of incorrect exposures, and this interferes with and/or slows down the workflow.

It is advantageous to minimize the time between making the record and the first opportunity for assessing it because this speeds up the decision as to whether the records are technically good or whether they may need to be repeated. Fast verification is thus a considerable aid to a better workflow.

FIG. 1 shows an X-ray diagnosis device which is known from German patent document DE 195 27 148 C1 having an X-ray tube 2 which is supplied with high voltage and heating voltage from a high-voltage generator 1 and which produces a conical X-ray beam 3, which passes through a patient 4 and produces beam images on an X-ray detector 5 which is sensitive to X-ray radiation 3. The output signal from the X-ray detector 5, the image data 6, is supplied to an imaging system 7. The imaging system 7 may have converters, image stores and processing circuits, and is connected to a monitor 8 for reproduction of the detected X-ray images. Control elements 9 are connected via a system controller and system communication 10 to the other components of the X-ray diagnosis device.

FIG. 2 shows a perspective cross section of the X-ray detector 5. The core components of the X-ray detector 5 comprise a solid-state pixel matrix, line drivers and amplifiers. The solid-state pixel matrix is composed, for example, of a layer with a scintillator 11, for example composed of cesium iodide (CsI), which, when illuminated by the X-ray radiation 3, feeds visible photons to a pixel matrix 12 composed of amorphous silicon, and these produce a visible X-ray image. Each of the pixels or picture points in the pixel matrix 12 comprises, as is shown on an enlarged scale in FIG. 2, a photodiode 13 and a switch 14, which is connected to row lines 15 and column lines 16. The pixel matrix 12 is applied to a glass substrate 20.

All of the pixels in a row are in each case addressed and read simultaneously by the line drivers 17. In the simplest case, an image is read progressively, line by line. The signals are supplied to a processing circuit 18, in which the signals are processed in parallel in a large number of amplifiers, are joined together by multiplexers, and are converted in an analog/digital converter (A/D converter) to a digital output signal for further digital processing.

The image information is converted in an X-ray converter, for example cesium iodide (CsI) by way of these solid-state detectors for X-ray imaging, which were developed some years ago and are based on active read matrices composed, for example, of amorphous silicon (a-Si). This image information is stored as an electrical charge in the photodiodes of the matrix, and is then read out and converted from analog to digital via an active switching element having dedicated electronics. These detectors, or else other digital detectors or detectors based on CCDs, are used to send an image directly to the imaging station, the imaging system 7 and the monitor 8, and it is thus in principle possible to produce an immediate image, which provides the recording technician or medical practitioner with the required feedback that the record is correct within a very short time (a few seconds).

However, in practice, the detector initially provides only a raw image, which cannot be viewed as such. A range of preprocessing steps, such as offset, gain and defect correction and postprocessing steps such as dynamic range matching, grey-scale mapping, grey-scale inversion, filtering of widely different types and windowing must be carried out in the imaging system 7 before the image is in the desired form and can be assessed. Since the image matrices for general digital radiography and mammography comprise several thousand pixels in both directions (for example 3000×3000 or more), large amounts of data need to be processed. If one does not wish to use special expensive hardware, times of 30 seconds or more are required with present-day standard PC-based technology—depending on the processing complexity. These long times are not acceptable. Since, in general, the complexity of the algorithms increases linearly with the improvement in computer performance, this problem will likely not be resolved.

European patent document EP 0 567 174 B1 discloses a method and an apparatus for reproducing X-ray images, in which the original data (raw images) are supplied to a digital processor, and as a security copy to a workstation, after logarithm formation and quantization, from a read apparatus for storing fluorescent materials. The image processor reduces the amplitude by clipping so that the images can be recorded on a film.

The images provided for recording are reproduced on a preview monitor. If the detected image is intended to be recorded just on one image, then this image is also reproduced completely, without reduction. If, on the other hand, a number of images are intended to be recorded like a mosaic on a film, then the number of pixels and hence the resolution of the images are correspondingly reduced. These mosaic images are reproduced on the preview monitor and, provided the viewer accepts the records, can be stored as a hard copy on the film in this reduced form.

SUMMARY OF THE INVENTION

The invention is based on the object of providing a method for operating an imaging system by using a large-area image detector of the type mentioned above that permits an assessment immediately after image production as to whether the record has been correctly exposed and includes the object completely.

According to the invention, the object is achieved by the following steps: converting the X-ray images into images with low resolution; processing the images with low resolution with images and/or parameters matched to the reduced resolution; immediately reproducing the images with low resolution; subsequently processing the X-ray images with parameters for full resolution, and reproducing the X-ray images with full resolution.

This method means that the individual preprocessing and postprocessing steps are considerably speeded up, with a low level of processing performance and a minimal amount of time involved, with the amount of data being reduced using suitable undersampling, so that images can be reproduced with low resolution on the monitor 8 in a very short time (for example, within a few seconds of the production of the X-ray images from the raw images); this makes it possible to see whether the record has all the features required for diagnosis, i.e., whether the record has been correctly exposed and contains the object completely.

According to the invention, preprocessing of the X-ray images with parameters for full resolution can be carried out at the first step. The X-ray images can be undersampled in order to convert the X-ray images, according to the invention, to images with low resolution. The parameters entered for preprocessing and image processing may advantageously be the images required for this purpose, parameters such as the sampling depth, the reduction factor as an integer, and the number of required images, etc.

Faster processing can be carried out if initial preprocessing is carried out for immediate reproduction of the images with low resolution and for reproduction of the images with full resolution, and by carrying out second preprocessing for the reproduction of the images with full resolution, after the immediate reproduction of the images with low resolution. Consequentially, the preprocessing for immediate reproduction of the images with low resolution means that some of the preprocessing steps can be omitted, for example, certain filter operations which are not required for an overview but are required and are retrieved for full resolution with diagnostic quality.

DESCRIPTION OF THE DRAWINGS

The invention is explained in more detail in the following text with reference to an exemplary embodiment, which is illustrated in the drawings.

DETAILED DESCRIPTION OF THE INVENTION

Figure 1:
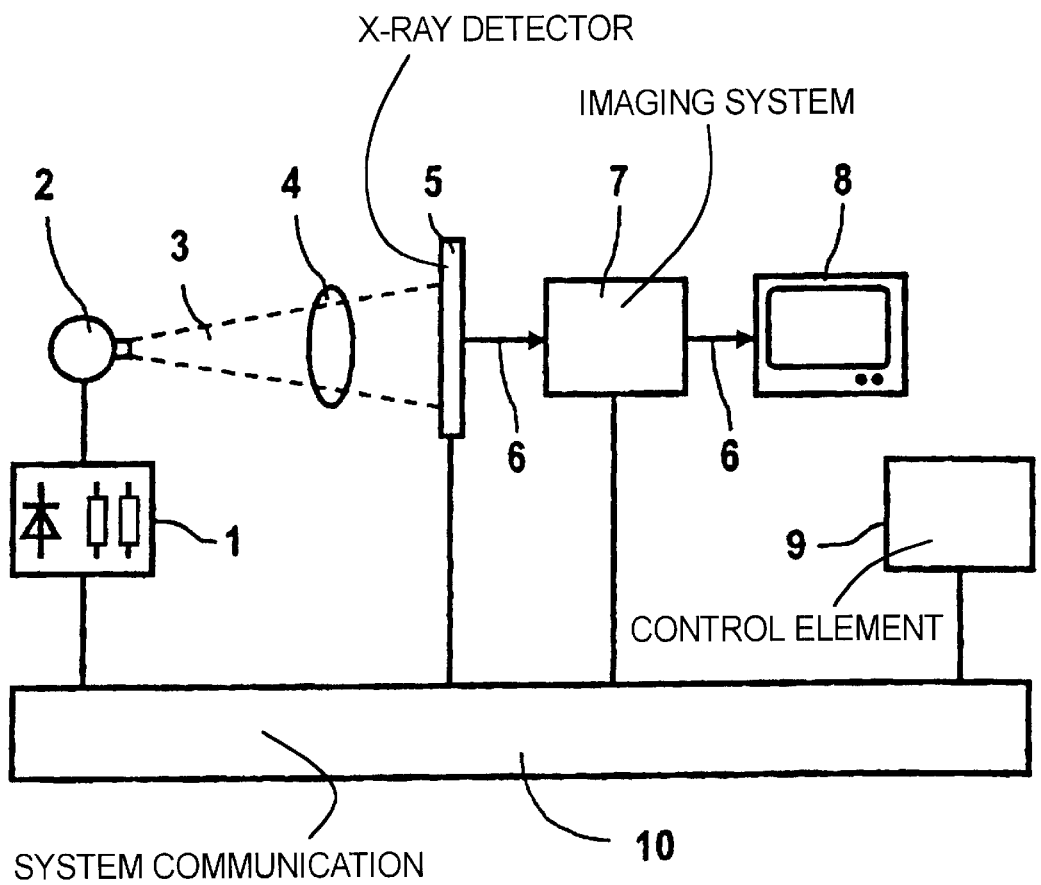
FIG. 1 is a schematic block diagram showing a known X-ray diagnosis device having one X-ray detector.
Figure 2:
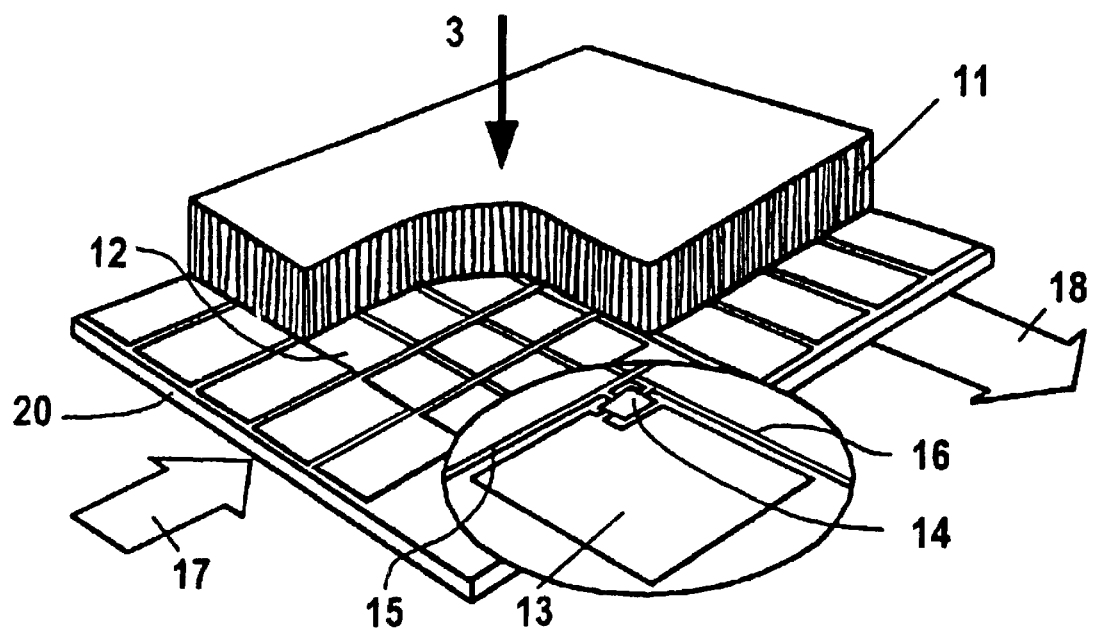
FIG. 2 is an orthoganal perspective view of a known X-ray detector.
Figure 3:
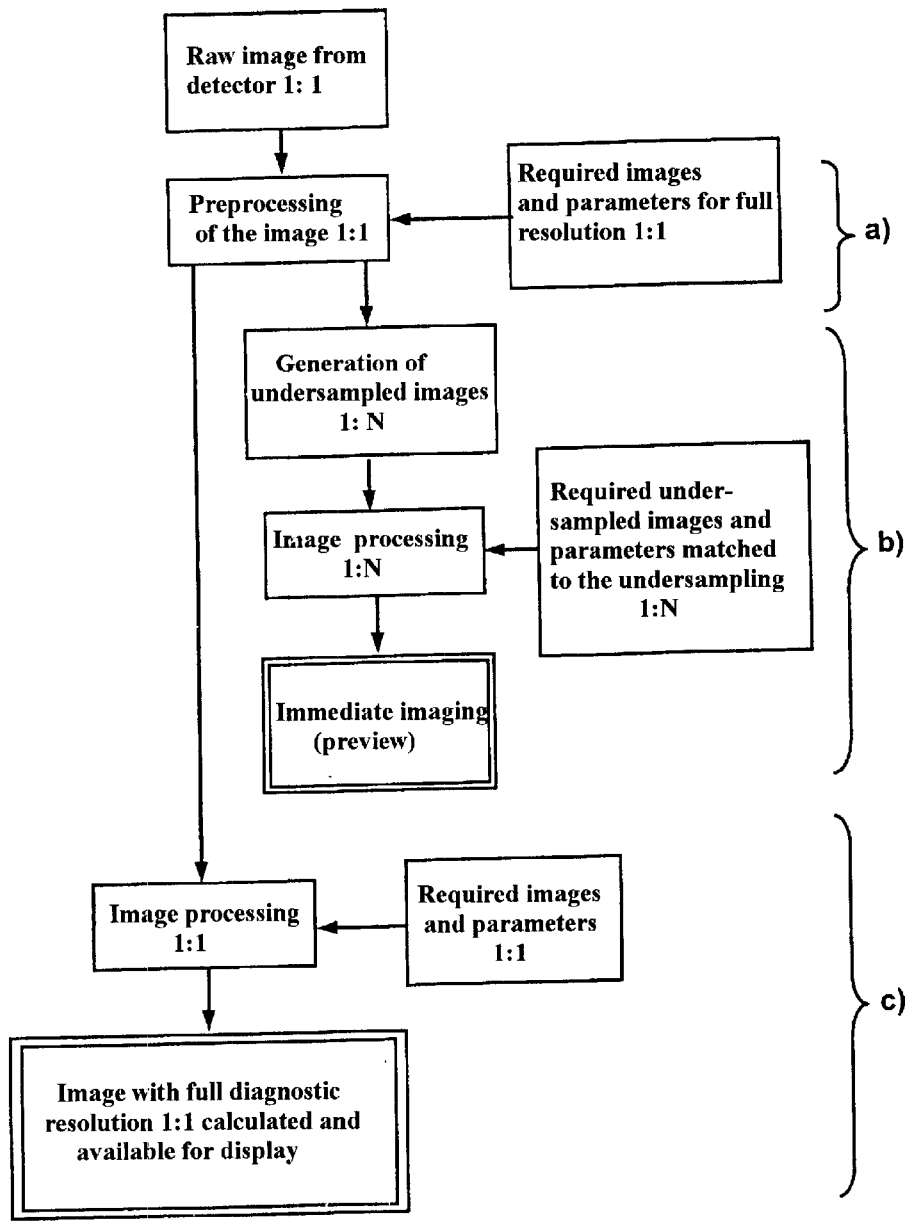
FIGS. 3 through 5 are flowcharts of the inventive method as carried out in the imaging system illustrated in FIG. 1.

FIG. 3 shows the time sequence for image processing in the computation unit in the imaging system 7. Starting from the raw image which is supplied from the detector 5, the image is preprocessed in a first step (a), if this is necessary and this process is not very time-critical, with the full 1:1 resolution. The images required for this purpose and the parameters for full 1:1 resolution are supplied to the preprocessing.

After this, in a second step (b), the processed raw image is sampled at a reduced sampling rate, in order to generate 1:N undersampled images. The number of undersampled images required and 1:N parameters matched to the undersampling are supplied in the subsequent 1:N image processing. After this, the immediate image, which is referred to as the preview, can be displayed immediately.

Only after this is the rest of the 1:1 image processing, which involves considerable computation effort and consumes a large amount of time, with the full diagnostic resolution being continued in the final step (c). The number of images and parameters required for full 1:1 resolution are supplied to the image processing. After this, the processed image is available to be displayed with the complete extent of the diagnostic 1:1 resolution.

Figure 4:
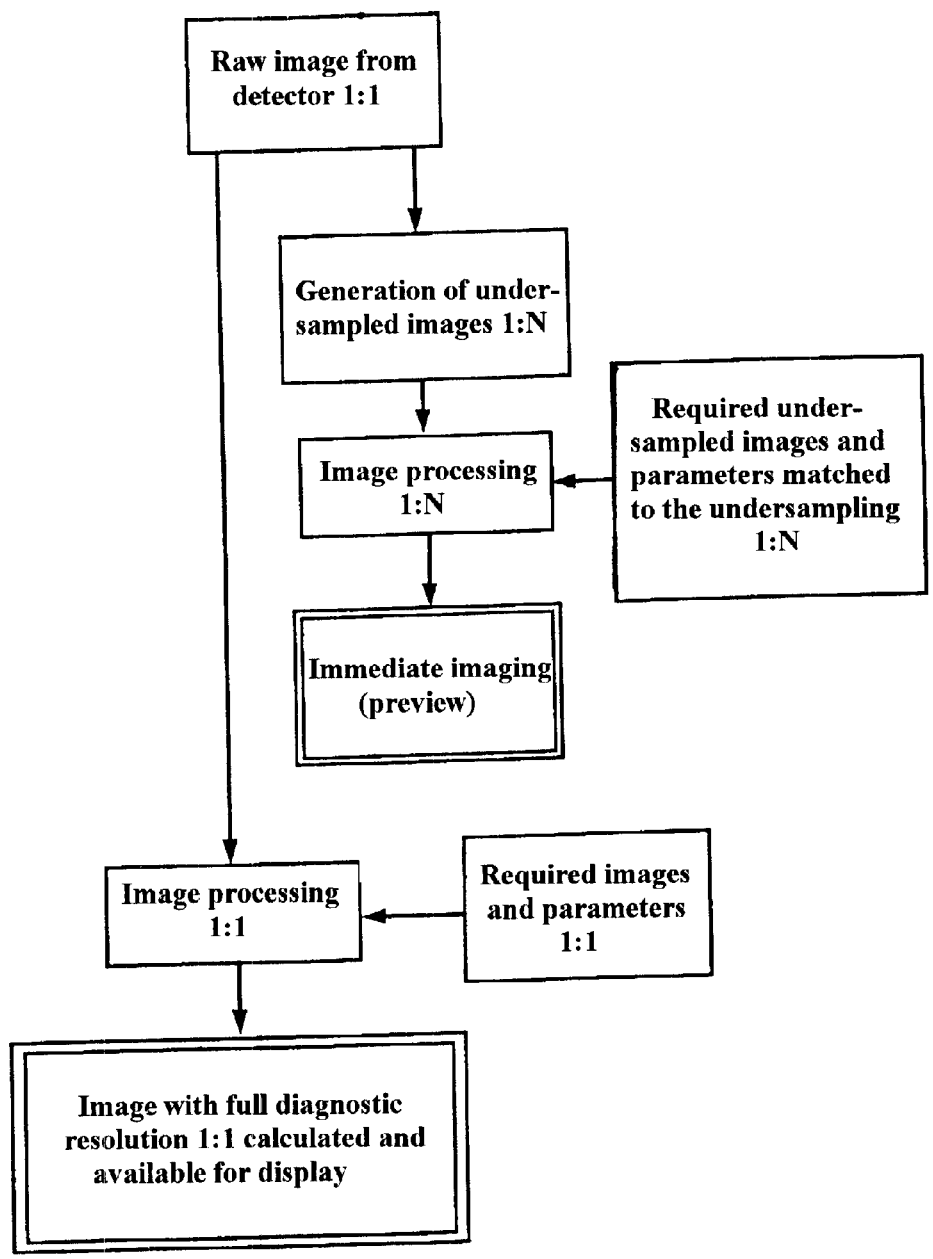

FIG. 4 shows the time sequence for simplified image processing in the computation unit in the image system 7. Starting from the raw image, which is supplied from the detector 5, an image with 1:N reduced resolution is produced directly. The number of undersampled images required and the 1:N parameters matched to the undersampling are one again supplied during the subsequent 1:N image processing. The immediate image is displayed directly after this.

The required complete image processing with high resolution is then continued. The number of require d images, and the parameters for full 1:1 resolution, are supplied to the image processing. After this, the processed image with full resolution can be reproduced on the monitor 8.

Figure 5:
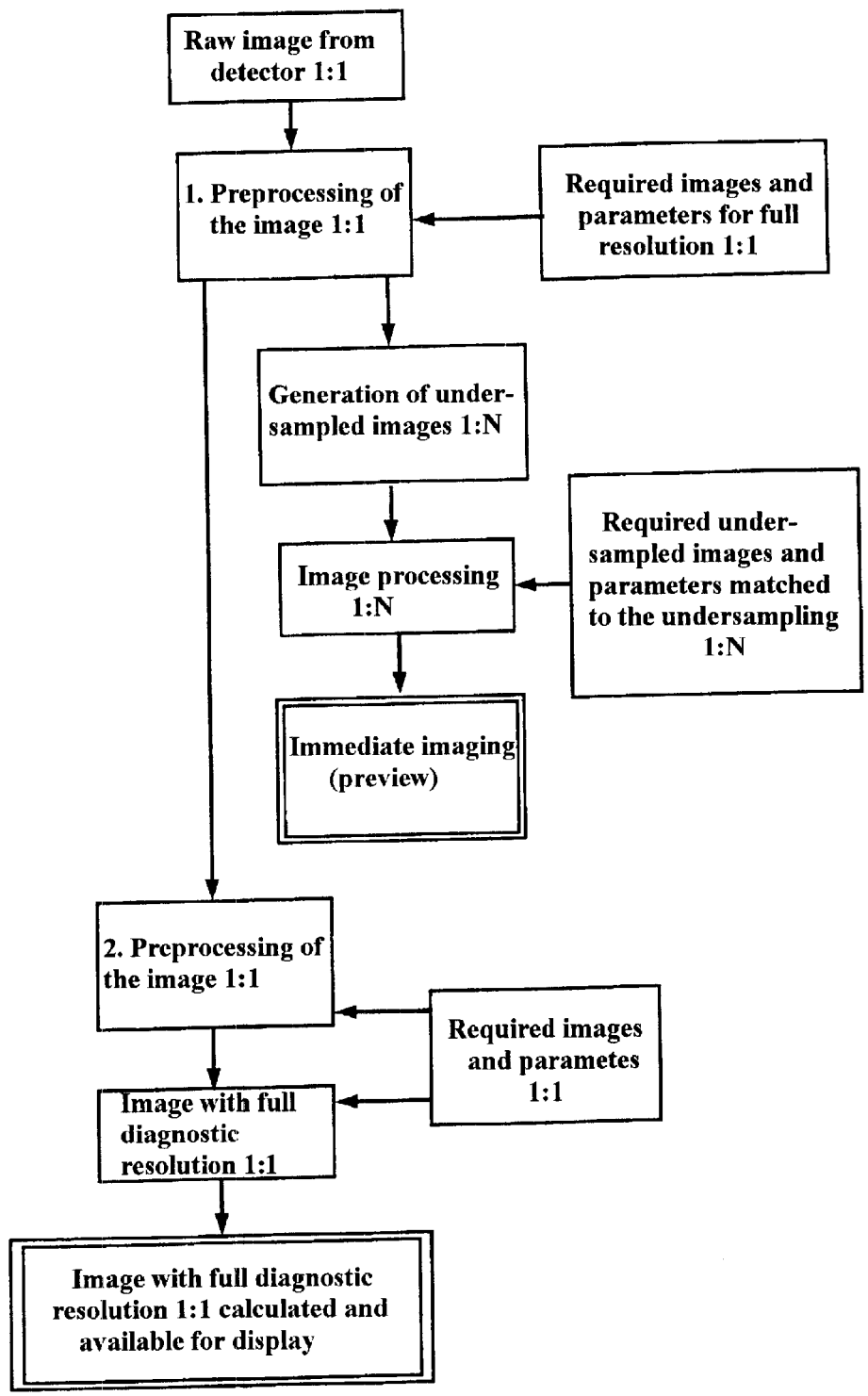

The time sequence of a further method according to the invention, which corresponds essentially to that illustrated in FIG. 3, is explained referencing FIG. 5. The only difference is that the preprocessing with high 1:1 resolution has been subdivided.

The raw image from the detector 5 is processed in a first preprocessing step with full 1:1 resolution using processing steps which are not very time-critical. The preprocessing is supplied with the images and parameters required for this purpose, for full 1:1 resolution.

An image with reduced 1:N resolution is then produced. The number of undersampled images required and the 1:N parameters matched to the undersampling are once again supplied during the subsequent 1:N image processing. The immediate image is displayed directly after this step.

The second part of the preprocessing, with the full 1:1 resolution, is then continued, and the required complete image processing with high resolution is then carried out. The required parameters for full 1:1 resolution are supplied to the preprocessing and to the image processing. The processed image with full resolution can then be reproduced on the monitor 8.

The method according to the invention for operating an X-ray diagnosis device with rapid immediate imaging using a preview allows the image processing to be carried out simply, i.e., without using costly special hardware. Furthermore, this method utilizes the fact that full resolution is not required to assess whether the object has been recorded completely and correctly exposed, so that an immediate image (preview) can be produced within a maximum of a few seconds. The immediate image is made possible in computation terms by using undersampling to considerably reduce the amount of data—for example, 1:3 undersampling on its own reduces the amount of data by a factor of virtually 10—so that the image processing can be speeded up.

In this case, the reduction in the image matrix and the undersampling can relate to each integer, such as reduction of 3000×3000 matrix to, e.g., 1500×1500, 1000×1000, or 750×750. The reduction is dependent on:

(i) the original image size, (ii) the complexity of the image processing, (iii) the performance of one or more of the computation units used in the imaging system 7, (iv) the desired resolution required for the preview image itself, and (v) the desired time for displaying the preview image.

In the 1:N undersampling, all of the images, i.e., the raw image and the images required for further image processing (e.g., the offset image, gain image, etc.) are likewise sampled in a corresponding manner. These further images may already exist, for example, from prior calibration. An exemplary 1:3 undersampling means that all the images (i.e., the raw image and the offset image, gain image, etc.) which originally had a matrix size of, for example, 3000×3000 are reduced to 1000×1000. Every second and third point in the x and y directions in the matrix is thus ignored. Each such reduced image comprises far fewer pixels, and each operation such as subtraction of the offset image from the raw image, multiplication of the gain image by the subtraction image, further filter operations, etc., are therefore carried out with far fewer pixels in the image, resulting in time improvements for immediate imaging.

The preprocessing and postprocessing functions can be carried out on software or on hardware, or partially on hardware and software.

The split in the image processing into the "preview path" and the "full-resolution-path" can, as shown in FIG. 4, be carried out directly after the detector has acquired the raw image; however, it may also be worthwhile to initially carry out less time-consuming preprocessing steps jointly, as shown in FIG. 3, before the branching.

In order to produce the preview image, parts of the image processing which are irrelevant to the preview image, such as edge prominence enhancement, can be omitted in order to further speed up the process.

The method according to the invention is based on the following principle. The full image resolution is not required to assess whether the record has been correctly exposed and the object is included completely, which is distinguished from the case where the full image resolution is required for diagnosis; with the reduced image, an exposure and inclusion assessment can be made—the individual preprocessing and postprocessing steps can be considerably speeded up in time (in a preview) by using suitable undersampling to reduce the amount of data, permitting display times of a few seconds or less. Since the diagnostic resolution is generally not required shortly after making the record, the calculation of the image with full resolution can be carried out subsequently.

The above-described method is illustrative of the principles of the present invention. Numerous modifications and adaptations will be readily apparent to those skilled in this art without departing from the spirit and scope of the present invention.

What is claimed is:

1. A method for operating an X-ray diagnosis device for producing X-ray images using an X-ray appliance, for processing said X-ray images using a computation unit, and for displaying said X-ray images using a reproduction apparatus, comprising the steps of:

converting said X-ray images into images with low resolution;

processing said images with low resolution with at least one of images and parameters that are matched to said low resolution;

immediately reproducing said images with low resolution;

subsequently processing said X-ray images with parameters for full resolution; and reproducing said X-ray images with full resolution.

2. The method as claimed in claim 1, further comprising the step of preprocessing said X-ray images with parameters for full resolution.

3. The method as claimed in claim 1, wherein said step of converting said X-ray images into images with low resolution comprises the step of undersampling said X-ray images.

4. The method as claimed in claim 1, wherein one of said parameters is a sampling depth for image preprocessing and image processing.

5. The method as claimed in claim 1, wherein one of said parameters for image processing with low resolution is a reduction factor that is an integer.

6. The method as claimed in claim 1, further comprising the steps of:

performing a first preprocessing for immediate reproduction of said images with low resolution and for reproduction of said images with full resolution; and performing a second preprocessing for reproduction of said images with full resolution after said immediate reproduction of said images with low resolution.

7. The method as claimed in claim 1, wherein a number of required images is entered as a parameter for preprocessing and image processing.

* * * * *